United States Patent
Zhang (10) Patent No.: US 10,550,416 B1
(45) Date of Patent: Feb. 4, 2020

(54) DETERMINATION OF MULTI-DIMENSIONAL LOCATION, SPECIES AND GENOMIC COPY NUMBER BY COMPARATIVE FLUORESCENCE IMAGING OF THREE STAINED MICROBIAL CULTURES INCLUDING A LOWER GENOMIC COPY NUMBER, SLOW GROWTH CULTURE

(71) Applicant: Pei Zhang, Boston, MA (US)

(72) Inventor: Pei Zhang, Boston, MA (US)

( * ) Notice: Subject to any disclaimer, the term of this patent is extended or adjusted under 35 U.S.C. 154(b) by 645 days.

(21) Appl. No.: 15/183,768

(22) Filed: Jun. 15, 2016

Related U.S. Application Data (60) Provisional application No. 62/175,514, filed on Jun. 15, 2015.

(51) Int. Cl.
| | | |
|---|---|---|
| *C12Q 1/02* | (2006.01) | |
| *G01N 1/30* | (2006.01) | |
| *G01N 15/14* | (2006.01) | |
| *G01N 21/64* | (2006.01) | |
| *G01N 15/10* | (2006.01) | |
| *G01N 15/00* | (2006.01) | |

(52) U.S. Cl.
CPC .............. *C12Q 1/02* (2013.01); *G01N 1/30* (2013.01); *G01N 15/1463* (2013.01); *G01N 21/6428* (2013.01); *G01N 21/6458* (2013.01); *G01N 2001/302* (2013.01); *G01N 2015/0065* (2013.01); *G01N 2015/1006* (2013.01); *G01N 2015/1486* (2013.01); *G01N 2021/6439* (2013.01); *G01N 2201/12* (2013.01)

(58) Field of Classification Search
None
See application file for complete search history.

(56) References Cited

PUBLICATIONS

Frigault, Melanie M., et al. "Live-cell microscopy—tips and tools." J Cell Sci 122.6 (2009): 753-767.*

* cited by examiner

*Primary Examiner* — G Steven Vanni (57) ABSTRACT

The present invention provides a microbial genomic analysis tool, named Spatial Analytical Microbial Imaging (SAMI), which provides the spatiotemporal and comparative intracellular ploidy, indicating the relative growth rate of the cells in situ. Firstly, pure cultures of two microbial species were pre-evaluated for their validity using SAMI. Secondly, the same pure cultures were split aliquot to pure culture and mixed culture, and grown concurrently to reduce error. Another set of pure culture can also be grown as a standard to evaluate inferential comparative genomic copy number if necessary. Thirdly, the genomes of individual cells in the pure culture and the mixed culture are stained with membrane permeable fluorescent DNA markers and analyzed by confocal laser scan microscopy and an image software. The average fluorescent intensity (AFI) and the total genomic fluorescent biding area (GFA) of slow growth pure cultures indicate the population AFI and GFA using inferential statistics. They are used as standards in comparison with the results of the mixed culture to specify the genera, 3D locus and the inferential comparative genomic copy number or a different category of each cell. Fourth, the final results are presented in 3D.

14 Claims, 9 Drawing Sheets
(4 of 9 Drawing Sheet(s) Filed in Color)

DETERMINATION OF MULTI-DIMENSIONAL LOCATION, SPECIES AND GENOMIC COPY NUMBER BY COMPARATIVE FLUORESCENCE IMAGING OF THREE STAINED MICROBIAL CULTURES INCLUDING A LOWER GENOMIC COPY NUMBER, SLOW GROWTH CULTURE

DESCRIPTION

FIELD OF THE INVENTION

The present invention relates to a method for analyzing a bacterial community using Spatial Analytical Microbial Imaging method.

BACKGROUND OF THE INVENTION

There is a lack of a generic tool in acquiring spatiotemporal and comparative genomic copy number in-situ for universal co-culture microbial community. Furthermore, many methods are limited to 2-dimensional (2D) observations. However, cells are in fact 3-dimensional (3D) structures and exist in 3D microbial consortia.

Some essential microbial cellular and community information are missing by most Molecular fingerprinting techniques. Denaturing Gradient Gale Electrophoresis (DGGE) (Muyzer, Waal, & Uitierlinden, 1993)(US7560236B62), clone libraries(US20140228223A1), T-RFLP (Terminal Restriction Fragment Length Polymorphism) methods, flow cytometry, Comparative genomic hybridization (CGH)(Pinkel et al., 1998)(Francisco, Kallioniemi, Waldman, & Francisco, 2000), DNA sequencing, real time-PCR(Pecoraro, Zerulla, Lange, & Soppa, 2011), need to destroy community structure and/or cellular integrity therefore ignore important info. such as spatial locus of cells and their in situ genomic copy number. Fluorescent In-situ hybridization (FISH) (US005880473A, US006136540A) maintains the cellular integrity, but lacks the genomic copy number and demands major efforts in developing specific fluorescent markers, which allow for limited applications.

The present invention overcomes the problems outlined above that provides the spatiotemporal and comparative intracellular ploidy that represents the growth rate of the cell (Akkermans, Elsas, & Bruijn, 1996). The present invention allows to maintain intact cell structures while identify the genera of the cells in the mixed culture and their 3D locus and intercellular structure. The present invention provides information of the relative genome size of the microorganisms in the mixture compare to those of their pure culture standards. The present method also provides relative metabolic growth rate of the cells and the spatiotemporal change of the community through inferential comparative genomic copy number evaluation. The invention presented makes it possible to compare standards of pure cultures with the mixed cultures to evaluate the growth of the cells within the mixtures and gain 3D information of the microbial community.

SUMMARY OF THE INVENTION

The present invention relates to microbial sample and standard preparation, staining and labeling, imaging and data acquisition as well as a computer-implemented method and apparatus for distinguishing objects of interest from other objects and background in an optical field. More particularly, the invention relates to a computer-implemented method of identifying, characterizing and counting objects in the 3D optical field which are tagged using fluorescence dye DNA binding to specifically visualize and semi-quantify the targeted objects in the sample. In particular, the invention relates to the use of such a computer-implemented method and apparatus for determining relative amplification rate of cells related to the copy of genomic compounds in the cell compare to that of the pure culture standards.

The present invention SAMI relates to the following embodiments 1 to 4:

1) Standard and culture preparation:

Pure culture standard need to be prepared at the same starting time and duration so that the sample culture was prepared under the same conditions and durations as the pure culture standards. In obtaining statistically valid data, sufficient number of cells need to be sampled in the pure culture standards in order to represent the population.

1.1) Pure culture growth standard

Pure culture standards with any particular growth rates of the targeted microorganisms shall be prepared at corresponding specific conditions to maintain certain quantity of genomic copy number of each strain. In one embodiment, slow growth pure culture standards are prepared under the condition of scarce nutrient to maintain low genomic copy number in the standards. Other methods, such as real time-PCR, fluorescence-activated cell sorting (FACS) analysis or radioactive labeling genome analysis can be used to quantify the exact copy numbers of the standards.

1.2) The targeted sample can be cultured or uncultured pure or mixed microorganisms in suspension or solid material. If it is cultured microorganisms, then the pure culture and the slow growth pure culture standards can be from different source. If it is uncultured microorganisms, the pure culture standards and the slow growth pure culture standards have to be isolated from the original flora but not necessarily to be sequenced or registered.

2) Staining and labeling of the sample.

2.1) Fixation:

Pure culture and slow growth pure culture Standards need to be fixed before to be evaluated as standards. The samples can be fixed or without fixation. Fixed sample are more stable with higher accuracy, but unfixed sample can show the temporal info. of the sample over certain time.

2.2) Florescent dye staining:

Membrane permeable fluorescent dye binding with AT or GC base pair are used for signaling the corresponding DNA fragment and semi-quantify the volume of the genome with 3D designation.

2.3) Imaging and data acquisition

Microscope preparation and photographing

Samples and standards were visualized by Confocal Laser Scanning microscope (CLSM). The optimal scan speed, pixel size and other parameters need to be set optimal. Imaging data were scanned through the third dimension, data were collected and transferred into a computer program, for example CLSM system software 3) Computer-implemented method for data analysis:

Images were analyzed in following procedure and logistics.

3.1) In both 2D and 3D data analysis, channels were split, thresholds were set to enclose most data point in a narrow range. The values, such as mean value, geometric center, binding area, were analyzed based on the original imaging data acquired by LSM 510 software.

3.2) Do the same process to mixed samples and concurrently grown pure cultures and the slow growth pure cultures.

3.3) Compare the average fluorescence intensity (AFI), mean value, of each cell in mixed culture to the mean value of the pure culture and identify the genera of each cell in the mixed culture image.

Figure 1:
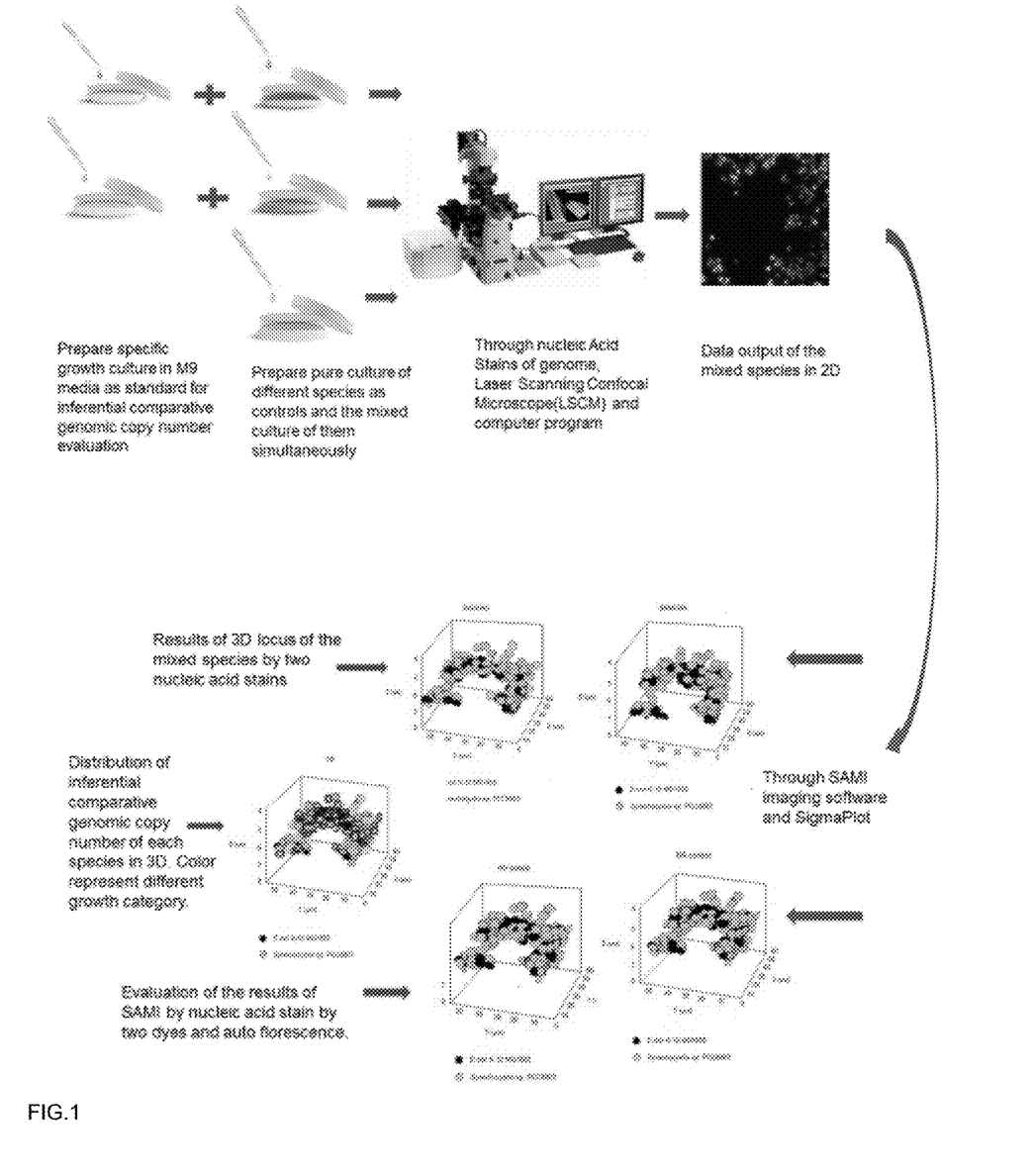
FIG. 1 Graphic summary of one embodiment of using Spatial Analytical Microbial Imaging (SAMI) to analyze a two species mixed community compare with pure culture standards.
Figure 2:
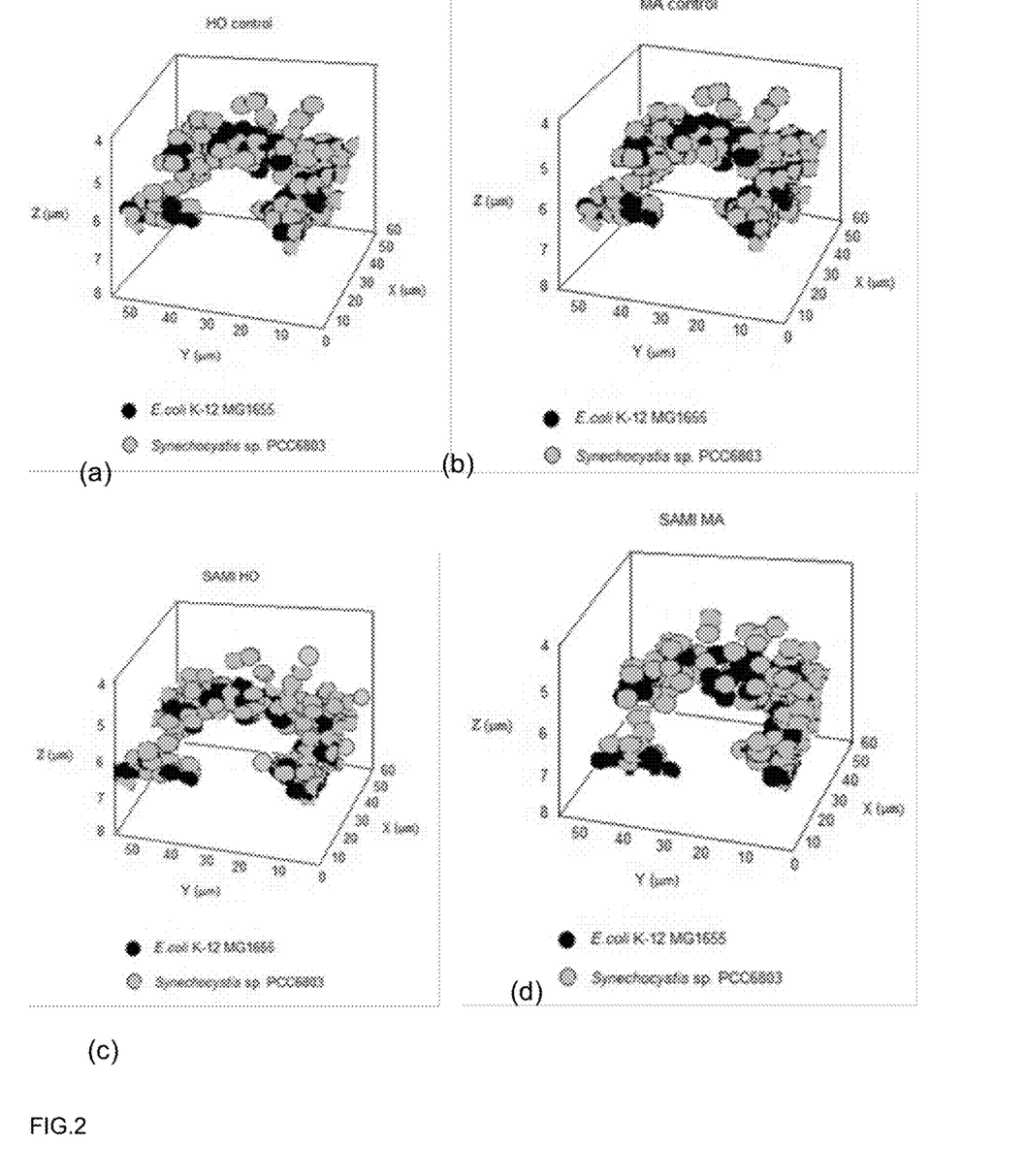
FIG. 2 In one imbodiment, the pure culture standards (also states as "control") and SAMI spatial distribution of the two species were shown in (a), (b) The controls represent the true spatial distribution of the two species in the sample by utilizing autofluorescence emitted by the one species. HO and MA stain the nucleic acid of all species. (c), (d) The spatial distribution of the two species via HO and MA nucleic acid staining using the SAMI method.
Figure 3:
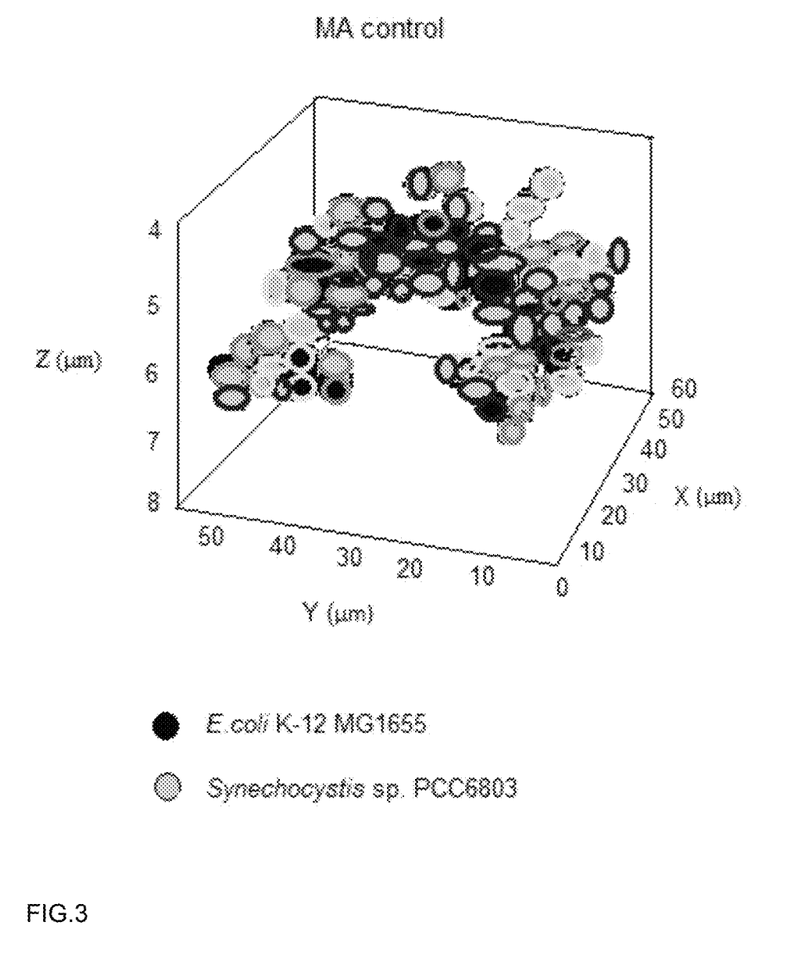
FIG. 3 In one example, 3D distribution of relative genomic copy number in the mixture of the two known species. Blue circles, represent the relatively faster growing cells, which have larger number of genomic copies than that of the growth standard. Green circles, represent equal growth cells with equal number of genomic copies as the growth standard. Yellow circles, represent the slower growth cells with less genomic copy than that of the growth standard. The growth standard can be the slow growing culture of oligoploid, merodiploid or polyploidy etc.
Figure 4:
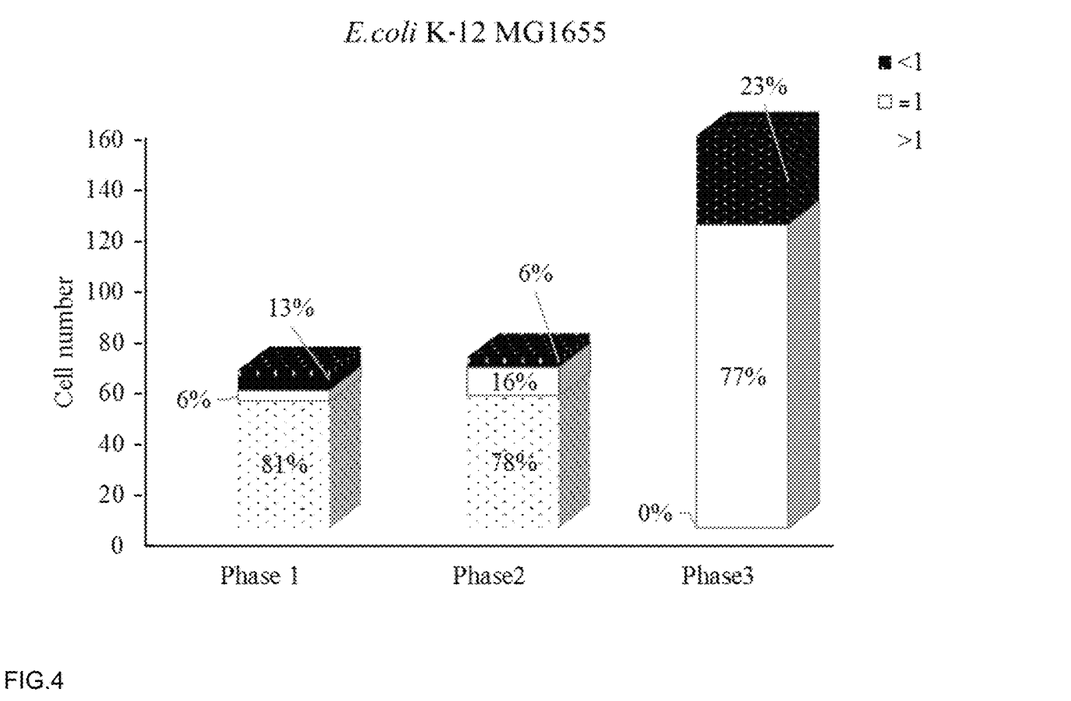
FIG. 4 Percentage distribution of inferential comparative genomic copy number of a species in the mixed culture at different time phases as explained in 1.5. The genomic copy number of each cell in the sample is evaluated by comparing the genome size with that of the growth standard with the genomic copy number of "1". The black bars represent the cells with lower genomic copy number than that of the standard, indicating slower growing cells. The white bars represent the cells with equal genomic copy number as the standard, hence indicating equal growth rate. The doted bars represent the cells with higher genomic copy number than the standard, indicating faster growing cells. The time interval between each phase is three days.
Figure 5:
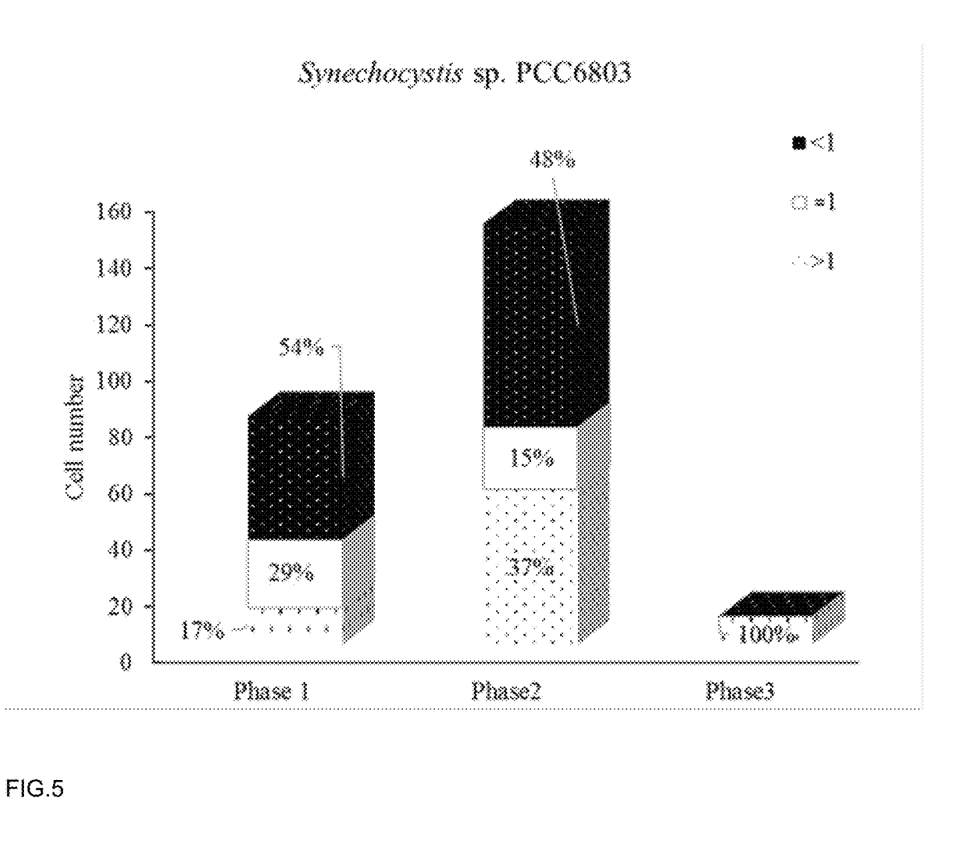
FIG.5 Percentage distribution of inferential comparative genomic copy number of another species in the mixed culture at different time phases. The genomic copy number of each cell in the sample is evaluated by comparing the genome size with that of the growth standard with the genomic copy number of "1". The black bars represent the cells with lower genomic copy number than that of the standard, indicating slower growing cells. The white bars represent the cells with equal genome copy number and growth rate as the standard. The doted bars represent the cells with higher genomic copy number than that of the standard, hence demonstrating a faster growth rate than the standard. The time interval between each phase was three days.
Figure 6:
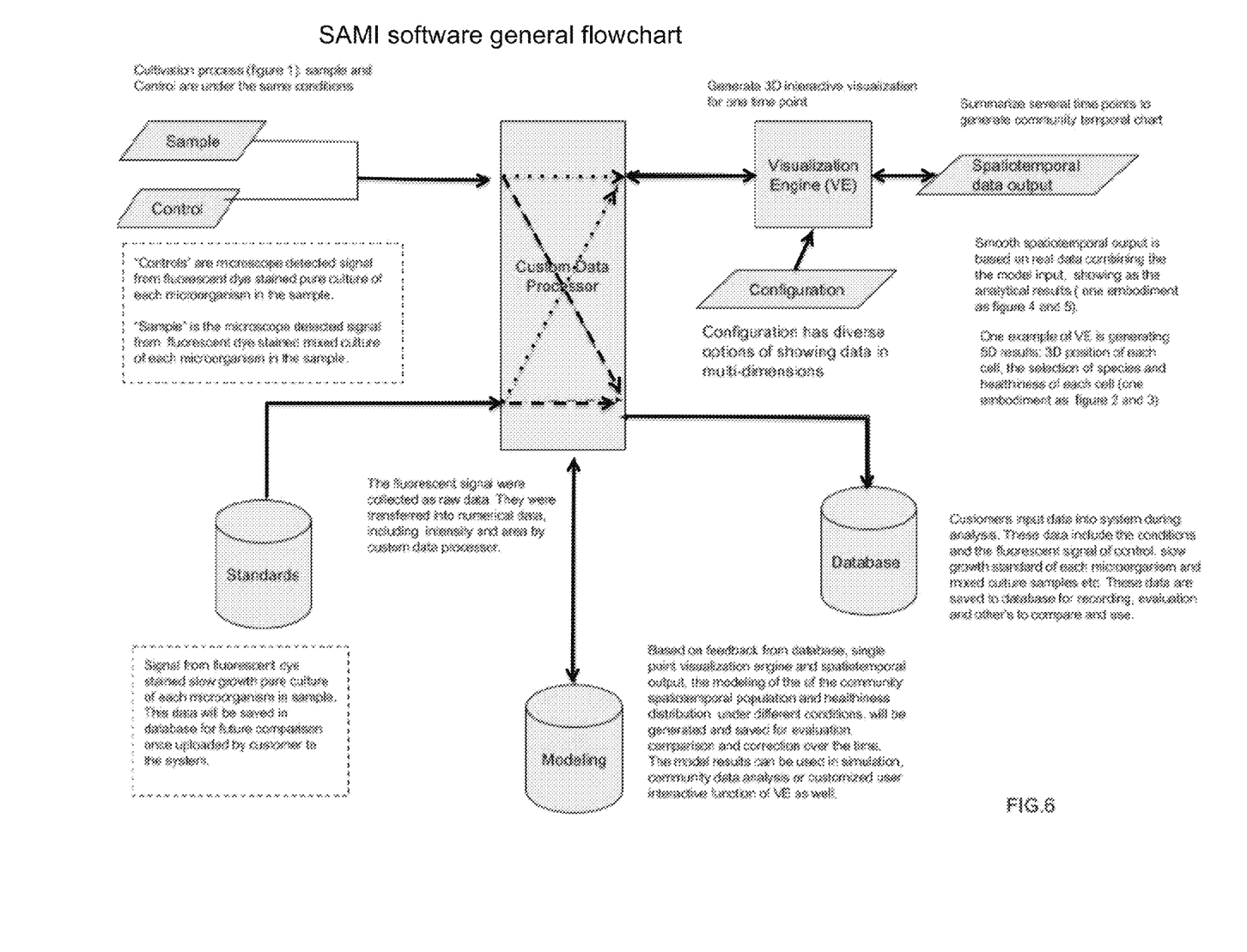
FIG.6 SAMI (Spatial Analytical Microbial Imaging) Software flowchart. The flowchart of process of using SAMI method combine with SAMI software in getting community spatiotemporal results is a system architecture. The system relationship among customer data input through software using or server, database build up, and modeling based on the mega-data from the database. The database and modeling results will become resources for customer to extract and utilize in evaluation, simulation, comparison or other data manipulation. Customer is able to extract data from database through customized user interactive function and display in Visualization Engine (VE).

3.4) Plot identified results using 3D data (x, y, z) in a software and compare with the control. The 3D distribution of the cells is as shown in FIG. 1.

[FIELD OF INVENTION] The present invention relates to an imaging tool for 3D in-situ spatial-temporal analysis of a pure or mixed culture microbial community.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Sample preparation, imaging and analysis
1) Culture preparation
1.1) pure culture standards preparation
Transfer a single colony of each pure culture into separate nutrient medium then incubate them at the desirable conditions. This solutions serve as pure culture standard solution.
1.2) mixed culture sample preparation
Mixture of the pure cultures should be cultivated by mixing the pure culture solutions explained at 1.1 together under certain conditions and each of the pure culture need to be cultivated again at the same time and conditions as the mixed culture to ensure they grow under the same condition with the same duration.
1.3) specific growth culture standard (growth standard).
In one embodiment, 1 ml of the pure culture solution, explained at 1.1, were transferred into a specific growth medium and cultivated for certain time under certain condition to maintain stable growth rate. The genomic copy number of the specific growth culture corresponding to the specific species and culture conditions does not necessarily have to be determined depend on different implementations. In some embodiments, the growth condition is used as criteria and/or relative growth rate compare to the growth standard is sufficient to evaluate the growth, then a relative growth rate will be used, therefore no need to invest the absolute genomic copy number. However, in other implement, if the genomic copy number of the growth standard is important, then genomic copy number of the specific growth culture can be determined by real time-PCR and fluorescence-activated cell sorting (FACS) analysis or radioactive labeling genome analysis.

2) Sample fixation, stain and preparation for imaging 2.1) Fixation

One embodiment of the detailed procedure is Samples were washed twice with buffer before fixation. In another embodiment, the fixation time used for mixed bacteria samples was 3 hours (Maruyama, et al., 2006). In one embodiment, the glass slides with samples on it were transported on a sterilized petri-dish in a biological hood and immersed in 1 ml of 4% buffered paraformaldehyde solution for 3 hours to fix the cells following by air drying. The buffered solution was made from stock paraformaldehyde (16% paraformaldehyde, CAS #30525-89-4, Electron Microscopy Sciences) in 2M NaCl and 0.1 M PBS buffer (15 mM MgCl2; 0.8 g sodium chloride, 0.2 g potassium chloride, 1000 ml sterile distilled water, pH 7.5)(Kowalchuk, et al., 2004). In the hood, the sample was covered in petri-dish at room temperature for 3 hours.

2.2) Fluorescent dye staining:

Fluorescent dye staining can be performed with membrane permeable dye binding to AT or GC base pair. In one embodiment, BisBenzimide H 33258(HO) is used. It is membrane-permeable and intercalates in A-T regions of DNA. An aliquot of 10 mg/ml Bisbenzimide H 33258, HO Solutions (DNA Quantitation Kit, DNA-Q, Sigma) was first diluted 10-fold with molecular biology grade water (W 4502, Sigma) to a concentration of 1 mg/ml. Another membrane-permeable dye be used in one embodiment is Mithramycin A (MA) (M6891Mithramycin A, Sigma) which is a natural polycyclic aromatic polyketide produced by various Streptomyces species, that preferentially binds to GC-rich sequences in DNA. In one embodiment, Mithramycin A solution was dissolved in methanol (MX0485-7 EMD) to form a 10 mg/ml solution. This solution was diluted 10 fold with 300 mM MgCl2 to form a 1 mg/ml stock solution. The working solution was made fresh every time by mixing MA stock solution, HO stock solution, 10X Fluorescent Assay Buffer (F 7171, Sigma) as well as 20 X MgCl2 and Molecular Biology Grade Water (W 4502, Sigma). The final concentration of MgCl2 was 15 mM at the time of measurement [9]. The dye solution was set under dark conditions at room temperature for 20 minutes to reach equilibrium. Then 1 ml of the mixed dye working solution was added to each sample for 20 minutes. In one embodiment, samples were washed once with buffer before staining.

3) Microscope preparation and imaging

For visible light and high numerical aperture objectives (>0.8) one embodiment of pixel size of ~0.1-0.2 µm is recommended [10]. In one embodiment, the pixel size of the CLSM system was optimized to 0.116 µm. In order to process fast dynamic scans, other embodiment of sequential raster scan was used and the scan speed was optimized at 0.9 µs/pixel to reduce delays between acquisitions. The other parameters were optimized and set up accordingly by using LSM 510 software. In one embodiment, these parameters were as follows: Amplifier offset at 0.1; Amplifier gain at 1; Power of 405 nm at 0.5 mW; Pinhole at 0.58 Airy equivalent; Optical slice 0.6 µm; Frame size at 512 µm×512 µm; Interval at 0.1 µm.

4) Image analysis using software 2D and 3D functions:

Both 2D and 3D data analysis, channels were split; thresholds were set to enclose most data point in a narrow range. The values, such as mean value, geometric center, binding area, were analyzed based on the original imaging data acquired by CLSM software and the results need to be displayed.

The same processes are done to the said mixed samples and concurrently grown pure cultures and the slow growth pure cultures.

Comparison of the average fluorescence intensity (AFI), mean value, of each cell in mixed culture to the mean value of the pure culture and identify the genera of each cell in the mixed culture image.

Figure 7:
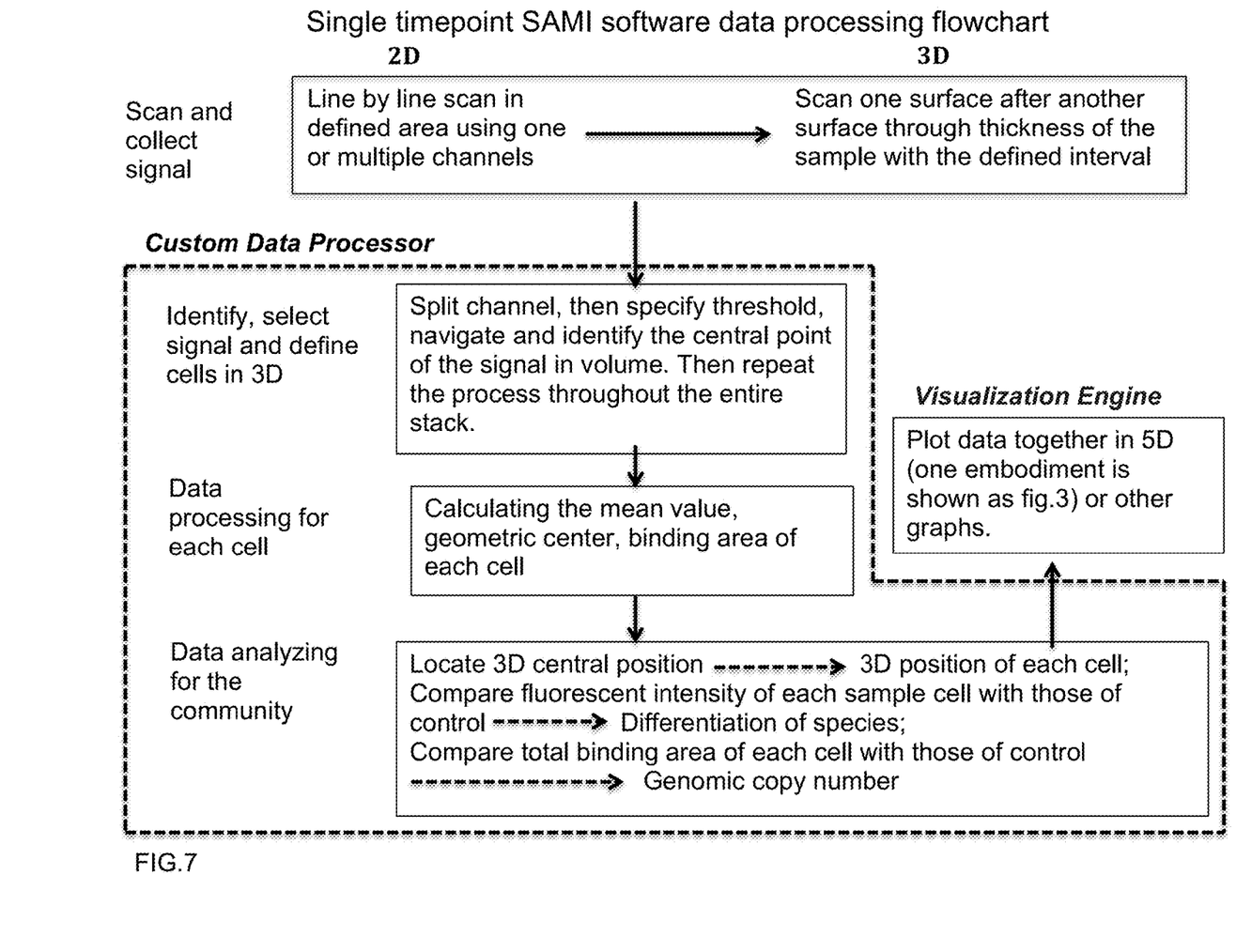
FIG. 7 Single time point SAMI software data processing flowchart. This chart explains the processing steps for one time point data, and the road map set forth for the various processes, computations and manipulations of the acquired 2D and 3D data that is acted upon mainly through custom data processor.
Figure 8:
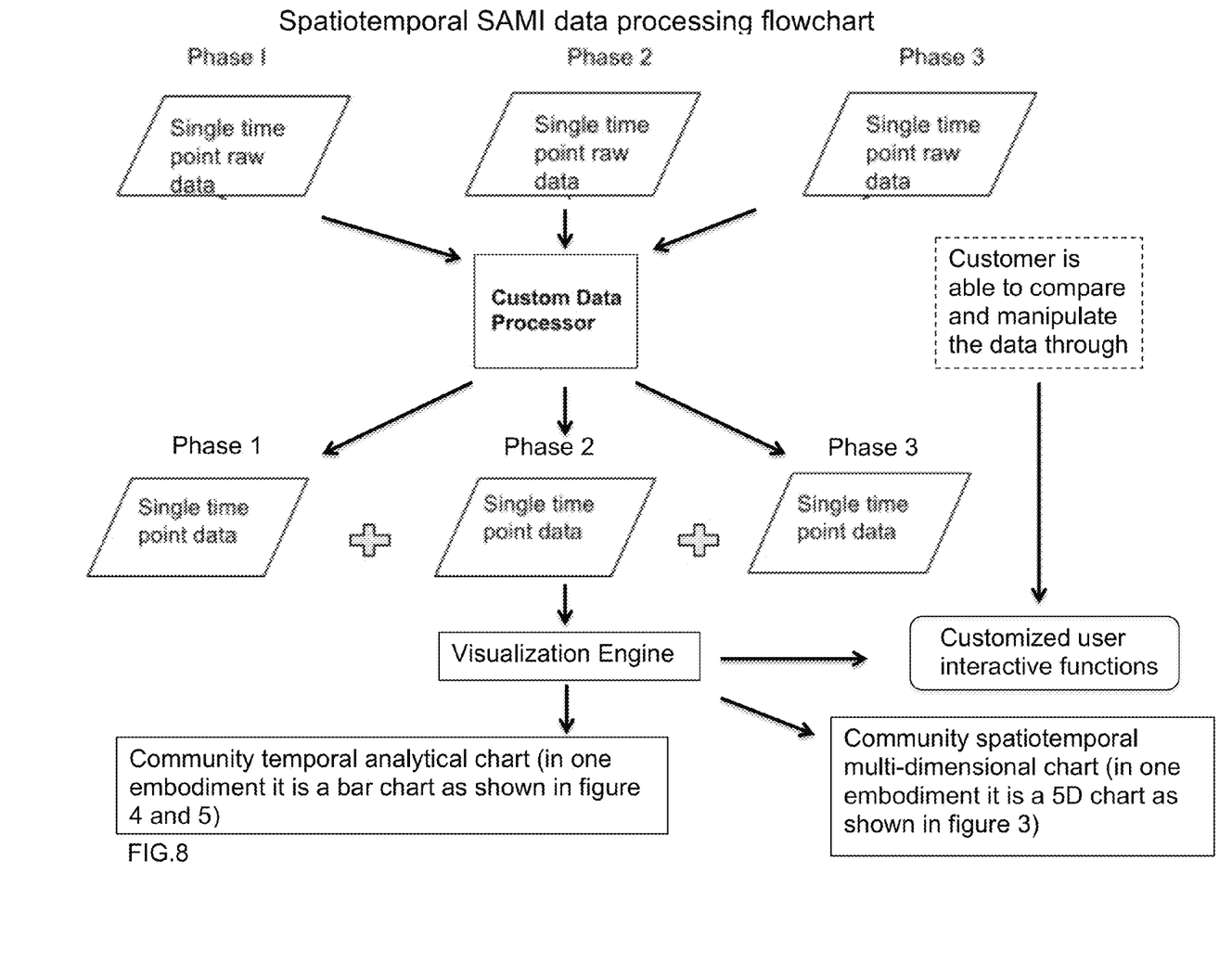
FIG. 8 Spatiotemporal SAMI software data processing flowchart. This flowchart explains the road map of how does the community temporal data generated based on single time point data. These results will be saved through communication with server in database for others use and modeling purpose. VE display data in multiple ways, one embodiment is bar chart, another embodiment is 5D diagraph. Customers can also utilize data from database or modeling results through interactive customized end user function to compare/manipulate with previous data or other's data.
Figure 9:
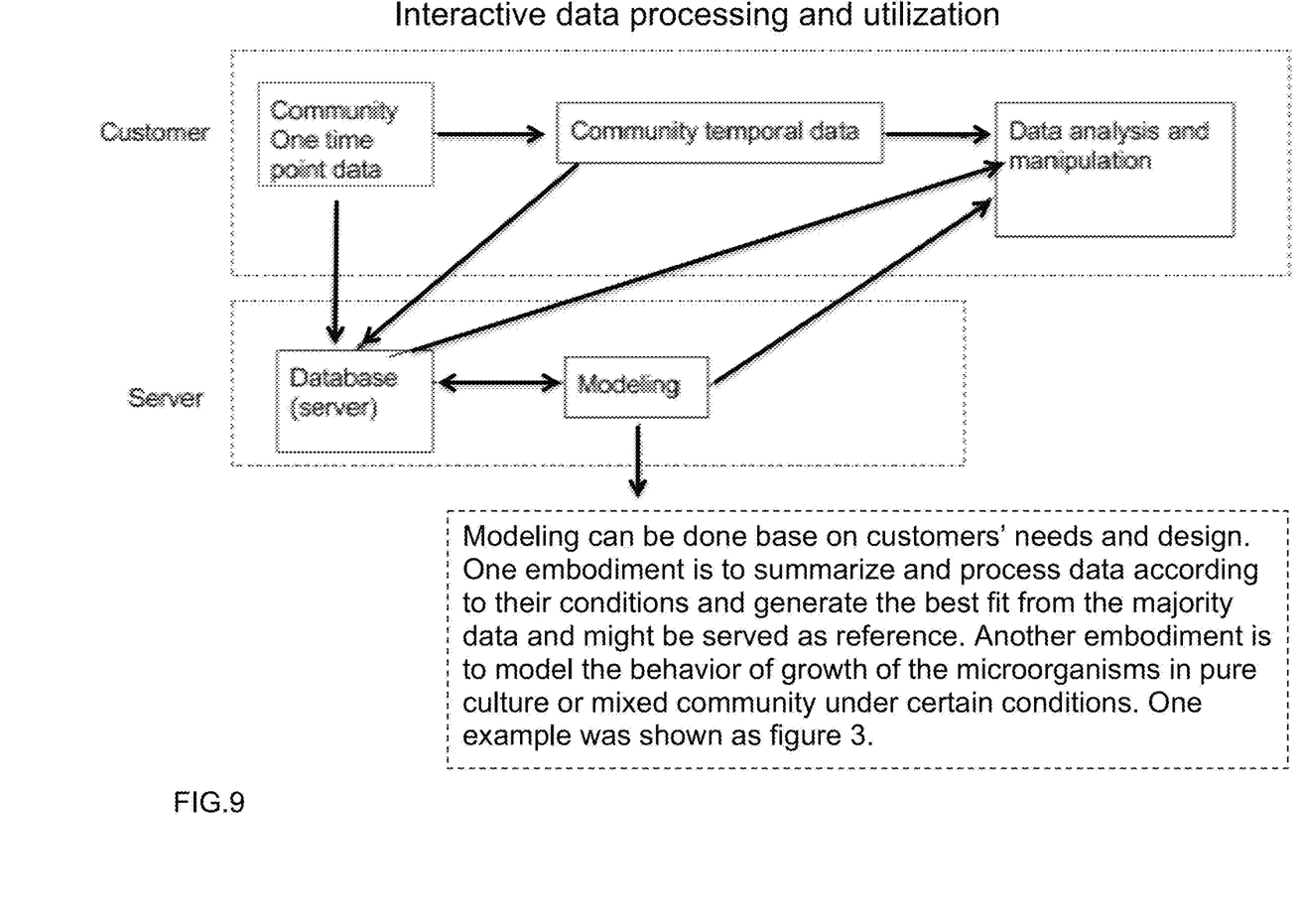
FIG.9 Interactive data processing and utilization. This figure explains the communication road map between customers and the server. Customer interact with server to transfer and acquiring data to share broader information in their data analysis. In the meantime, their data is also saved in server as part of the database for modeling and utilize by others. Modeling can be done based on customers needs and design, one embodiment is to summarizes data according to their conditions and process the best fit from the majority data as reference for community analysis.

Comparison of the total genomic fluorescent binding area (GFA) of the cells in the said mixed culture to the average value of the said slow growth pure culture standard of the same species. Calculate the genomic copy number of each cell of the said mixed culture sample and plot the data in 3D as shown in FIG. 7.

EXAMPLE 1

1) Culture preparation 1.1) To prevent contamination, E.coli K-12 MG1655 was transformed by inserting ampicillin resistant genes (AmpR) through electroporation. The size of the ampicillin resistant gene was approximately 1.25 kb[5], which is not significant in comparison to the whole genome size of E.coli K-12 MG 1655.

1.1.1) Pipette 40 µl of electro-competent cells (E.coli K-12 MG 1655) into ice-cold sterile 0.5 ml microfuge tubes. Place the cells on ice, as well as electroporation cuvettes.

1.1.2) Add 10 ng to 25 ng of DNA plasmid (1-2 µl) to each microfuge tubes and incubate in ice for 30 to 60 seconds, including controls.

1.1.3) Set the electroporation apparatus to electrical pulse of 25 µF capacitance, 2.5 kV, and 200 Ω resistance.

1.1.4) Pipette the DNA/cell mixture into the cold cuvette, tap the solution to ensure bacteria cell touch the bottom of the cuvette. Dry outside of the cuvette, put it into the device then push the pulse bottom.

1.1.5) Remove the cuvette and add 1 ml of LB media at room temperature as soon as possible.

1.1.6) Transfer the cells to a 17×100 mm polypropylene test tube, incubate under 37° C. for 1 hour.

1.1.7) Plate 50 µl, 100 µl, 150 µl, 200 µl of the electroporation cells onto the LB agar medium place containing 20 mM MgSO4, and 200 µg/ml ampicillin.

1.1.8) Wait until the liquid is absorbed and then invert the plate and incubate in 37° C. for 12-16 hours.

1.2) E.coli K-12 MG 1655 pure culture 1.2.1) Transfer a single colony of E.coli K-12 MG 1655 from an LB agar plate into a 50 ml sterilized polypropylene tube containing 25 ml LB solution supplemented with 25 µl of 200 µg/µl ampicillin sodium salt (69523, Sigma).

1.2.2) Incubate the tube in an incubator shaker (Fisher scientific isotemp. E-class incubator) at 225 rpm and 37° C. for 12 hours.

1.3) E.coli K-12 MG 1655 pure culture standard 1.3.1) One ml of E.coli K-12 MG 1655 culture was transferred from the incubator shaker to an alcohol sterilized glass slide, then placed in a petri-dish and kept at room temperature (27° C.±1° C.).

1.3.2) Two ml of freshly made BG-11 media was added daily onto the glass slide for three days to support E.coli K-12 MG1655 pure culture growth on the glass surface, which was kept under the same conditions as the mixed culture.

1.4) Synechocystis sp. PCC 6803 pure culture 1.4.1) One colony of Synechocystis sp. PCC 6803 from a BG-11 agar plate was transferred into 25 ml BG-11 media in a 50 ml sterilized polypropylene tube in a UV sterilized biological hood.

1.4.2) The tube was set under laboratory room light at room temperature (27° C.±1° C.) to allow synechocystis Sp.PCC6803 to grow in suspension.

1.4.3) Synechocystis sp. PCC 6803 pure culture standard 1.4.4) One ml of suspended Synechocystis sp. PCC 6803 culture was transferred onto an alcohol sterilized glass slide (as explained in E.coli pure culture) in a UV sterilized biological hood.

1.4.5) Two ml of BG-11 media was added on the glass slide every day for three days to allow the growth of the Synechocystis sp. PCC 6803 pure culture on the glass surface.

1.4.6) Mixed culture preparation

E.coli K-12 MG1655 was first cultivated on a glass slide surface for three days as described earlier as for the pure culture control. Then 1 ml of pure culture Synechocystis sp. PCC 6803 suspension was added onto the E.coli K-12 MG1655 glass slide located in the sterile petri-dish to allow the growth of both bacterial species as phase I. 2 ml of BG-11 media was then added to the glass slide every day for three days as phase 2. and the mixture was allowed to grow at room temperature (27° C.±1° C.) for another three days as phase 3. Pure culture controls of Synechocystis sp. and E.coli K-12 MG1655, were prepared concurrently.

Firstly a single colony of E.coli K-12 MG1655 was carefully isolated from the LB agar plate and transferred to 10 ml M9 media. The culture was then incubated in a shaker (Fisher scientific isotemp. E-class incubator) at 225 rpm, 27° C.±1° C. for 3 days. Ten 1 ml of the solution were then transferred into 10 ml of fresh M9 media and grown under the same conditions for 3 more days. This process was repeated a minimum of 3 times in order to obtain a slow growth culture standard.

1.4.8) Synechocystis sp. PCC 6803 slow growth culture standard

It has been previously reported that Synechocystis sp. PCC 6803 motile wild type has about 60 genomes per cell in stationary phase and this number varies for different strains [6]. The genome of Synechocystis sp. PCC 6803 slow growth pure culture was first investigated and inferential statistics were used in comparative genomic analysis to obtain comparative genomic copy number of each Synechocystis sp. PCC 6803 in the mixture sample.

A single colony of Synechocystis sp. PCC 6803 was transferred from an LB agar plate to 10 ml of BG-11 media. The culture grew for 3 days under room light and room temperature (27° C.±1° C.). 1 ml of it were then transferred into 10 ml of fresh BG-11 media and allowed to grow for 3 more days. The process was repeated 3 times. Inferential statistical analysis was used in obtaining genomic copy number standard of the slow growth cells. The absolute genomic copy number of the slow growth pure culture can be quantified by real-time PCR or a spectroscopic method.

2) Sample fixation, stain and preparation for imaging 2.1) Fixation

Because the nucleic acid dyes utilized in this study were membrane-permeable, samples could be fixed for one point sampling or processed without fixation for sequential sampling. The temporal observation of samples was performed without fixation. When fixation was utilized, samples were washed twice with buffer and then fixed for 3 hours in glass slides [7]. The glass slides were then transported on a sterilized petri-dish to a biological hood and immersed in 1 ml of 4% buffered paraformaldehyde solution for 3 hours at room temperature. The buffered solution was made from stock paraformaldehyde (16% paraformaldehyde, CAS #30525-89-4, Electron Microscopy Sciences) in 2M NaCl and 0.1M PBS buffer (15 mM MgCl2; 0.8 g sodium chloride, 0.2 g potassium chloride, 1000 ml sterile distilled water, pH 7.5).

2.2) Fluorescent dye staining

Fluorescent dye staining was performed with BisBenzimide H33258(HO) which is membrane-permeable and-intercalates in A-T regions of DNA. An aliquot of 10 mg/ml Bisbenzimide H 33258, HO Solutions (DNA Quantitation Kit, DNA-Q, Sigma) was first diluted 10-fold with molecular biology grade water (W 4502, Sigma) to a concentration of 1 mg/ml. Another membrane-permeable dye utilized in this study was Mithramycin A (MA) (M6891Mithramycin A, Sigma) which is a natural polycyclic aromatic polyketide produced by various Streptomyces species, that preferentially binds to GC-rich sequences in DNA. Mithramycin A solution was dissolved in methanol (MX0485-7 EMD) to form a 10 mg/ml solution. This solution was diluted 10 fold with 300 mM MgCl2 to form a 1 mg/ml stock solution. The working solution was made fresh every time by mixing MA stock solution, HO stock solution, 10X Fluorescent Assay Buffer (F 7171, Sigma) as well as 20 X MgCl2 and Molecular Biology Grade Water (W 4502, Sigma). The final concentration of MgCl2 was 15 mM at the time of measurement. The dye solution was set under dark conditions at room temperature for 20 minutes to reach equilibrium. Then 1 ml of the mixed dye working solution was added to each sample for 20 minutes. The quantification of DNA has been reported to require a high salt concentration[9]. Higher salt concentrations appear to cause the dissociation of proteins from DNA, allowing better binding of the dye molecules with AT or GC base pairs in minor groove of DNA. For peak fluorescence, at least 200 mM NaCl is required for purified DNA and 2.0 to 3.0 M for crude samples. Mg2+ ions have no effect on the assay in the final concentration range from 0.5 mM to 0.1 M and the salt concentrations of 3 M NaCl will not affect the assay. Samples were washed once with buffer before staining. The two dyes were combined and stained once for all the samples. The composition of mixed dye of HO and MA is shown in Table 1.

TABLE 1

Components of mixed dye of HO and MA

| Dyes | HO | MA |
| --- | --- | --- |
| 1 mg/ml dye | 5 µl | 5 µl |
| 20*MgCl2 | — | 0.16 ml |
| 10* buffer (5 mM Tris-HCl, pH 7.6, 8 mM NaCl) | 0.5 ml | 0.5 ml |
| Sterile water | 3.83 ml | |
| Total | 5 ml | |

Results are shown as FIGS. 1 to 4.

3) Microscope preparation and imaging

For visible light and high numerical aperture objectives (>0.8) a pixel size of ~0.1-0.2 µm is recommended [10]. In one embodiment, the pixel size of the CLSM system was optimized to 0.116 µm. In order to process fast dynamic scans, Sequential raster scan was used and the scan speed was optimized at 0.9 µs/pixel to reduce delays between acquisitions. The other parameters were optimized and set up accordingly by using LSM 510 software. In one embodiment, these parameters were as follows: Amplifier offset at 0.1; Amplifier gain at 1; Power of 405 nm at 0.5 mW; Pinhole at 0.58 Airy equivalent; Optical slice 0.6 µm; Frame size at 512 µm×512 µm; Interval at 0.1 µm.

4) Image analysis using software 2D and 3D functions:

As shown in FIG. 7, Both 2D and 3D data analysis, channels were split; thresholds were set to enclose most data point in a narrow range. The values, such as mean value, geometric center, binding area, were analyzed based on the original imaging data acquired by CLSM software.

The same processes are done to the said mixed samples and concurrently grown pure cultures and the slow growth pure cultures.

Comparison of the average fluorescence intensity (AFI), mean value, of each cell in mixed culture to the mean value of the pure culture and identify the genera of each cell in the mixed culture image as explained in custom data processor in FIG. 7.

Compare the total genomic fluorescent binding area (GFA) of the cells in the said mixed culture to the average value of the said slow growth pure culture standard of the same species. Calculate the genomic copy number of each cell of the said mixed culture sample. These data can be used to display single point time community distribution or in community temporal results in VE.

SAMI methods were mostly explained in FIGS. 1 to 5 and the SAMI software, system architecture and the road map of the various processes, computations and manipulations of information are shown in FIGS. 6 to 9.

What is claimed is:

1. A method of spatial analytical microbial imaging comprising:
   growing a plurality of cultures, including a target microorganism culture, a slow growth microorganism culture, and a control microorganism culture, wherein cells of the slow growth microorganism culture have a lower genomic copy number than a genomic copy number of cells of the control microorganism culture, wherein each of the plurality of cultures are grown under a set of conditions, the set of conditions being substantially the same for the control microorganism culture and the target microorganism culture and including a time period, the time period being, for the control microorganism culture and the target microorganism culture, concurrent and of the same duration;
   staining each of the plurality of cultures at an end of the time period with a fluorescent dye;
   imaging each of the plurality fluorescent stained cultures with a microscope and determining from the imaging an average fluorescent intensity for the targeted microorganism culture, a total fluorescent binding area for the targeted microorganism culture, an average fluorescent intensity for the control microorganism culture, and a total fluorescent binding area for the slow growth microorganism culture;
   comparing the average fluorescent intensity of the targeted microorganism culture to the average fluorescent intensity of the control microorganism culture and comparing the total fluorescent binding area of the targeted microorganism culture to the total fluorescent binding area of the slow growth microorganism culture; and
   plotting data from each comparing step on a multi-dimensional graph and determining a multi-dimensional location, a species, and a genomic copy number of the targeted microorganism culture.

2. The method of spatial analytical microbial imaging of claim 1, further including repeating the growing, staining, imaging, comparing and plotting steps for each of the plurality of cultures for a plurality of growth time periods, comparing and integrating the data and displaying results from the plurality of growth time periods on the multi-dimensional graph.

3. The method of spatial analytical microbial imaging of claim 1, wherein the set of conditions includes a volume of a growth media, a composition of the growth media, a frequency of feeding the microorganisms, a light intensity, and an incubation temperature, a starting time point, an ending time point, and a duration of incubation time.

4. The method of spatial analytical microbial imaging of claim 1, wherein the imaging includes a specific single channel or multi-channel/multi-track scanning program having a scan speed and a pixel or voxel size in multi-dimensions.

5. The method of spatial analytical microbial imaging of claim 1, wherein the slow growth culture is a standard against which the genomic copy number of cells in the target microorganism culture is evaluated.

6. The method of spatial analytical microbial imaging of claim 1, wherein the slow growth culture is quantified for an absolute genomic copy number using real time-PCR.

7. The method of spatial analytical microbial imaging of claim 1, wherein the slow growth culture is quantified for an absolute genomic copy number using fluorescence-activated cell sorting analysis or radioactive labeling genome analysis.

8. The method of spatial analytical microbial imaging of claim 1, further including determining an average fluorescence intensity of each cell of the control microorganism culture and determining whether there is a significant difference between the average fluorescence intensity of the control microorganism culture.

9. The method of spatial analytical microbial imaging of claim 8, further including, when the difference between the average fluorescence intensity of cells in the control microorganism culture is significant, comparing an average fluorescence intensity of each cell in the target microorganism culture to the average fluorescence intensity of each of the control microorganism culture, and identifying a genera of each cell in a multi-dimensional image of the target culture.

10. The method of spatial analytical microbial imaging of claim 1, further including comparing a total genomic fluorescent binding area of each cell in the target culture to an average value of total genomic fluorescent biding area of the slow growth culture, wherein a genomic copy number is set as one unit in order to facilitate comparisons.

11. The method of spatial analytical microbial imaging of claim 1, further including determining a genomic copy number of each cell of the target culture and plotting a location of each cell, a microorganism identification, and a genomic copy number of each cell in a multi-dimensional display.

12. The method of spatial analytical microbial imaging of claim 1, further including, prior to the step of growing the plurality of cultures, growing the slow growth microorganism culture in a medium designed for very slow culture growth for more than three days, transferring a 1× volume of the slow growth microorganism culture into a 10× volume of the slow growth medium, growing the slow growth microorganism culture for more than three days, repeating the growing, transferring, and growing steps at least three times.

13. The method of spatial analytical microbial imaging of claim 1, wherein the staining step includes not fixing the plurality of cultures and wherein the fluorescent dye is a membrane permeable binding dye.

14. The method of spatial analytical microbial imaging of claim 1, further including 2-dimensional and 3-dimensional data analysis, splitting channels, setting thresholds, calculating values based on imaging data acquired by the microscope, and displaying results in multi-dimensions.

* * * * *